US009782758B2

(12) United States Patent
Ghosh et al.

(10) Patent No.: US 9,782,758 B2
(45) Date of Patent: *Oct. 10, 2017

(54) METHOD OF PREPARING HYDROCARBON AROMATIZATION CATALYST, THE CATALYST, AND THE USE OF THE CATALYST

(71) Applicant: Saudi Basic Industries Corporation, Riyadh (SA)

(72) Inventors: Ashim Kumar Ghosh, Houston, TX (US); Scott Stevenson, Houston, TX (US); Meghan Simmons, Katy, TX (US); Michael Mier, Waller, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 661 days.

This patent is subject to a terminal disclaimer.

(21) Appl. No.: 13/868,296

(22) Filed: Apr. 23, 2013

(65) Prior Publication Data

US 2014/0316179 A1 Oct. 23, 2014

(51) Int. Cl.
| | |
|---|---|
| *B01J 29/44* | (2006.01) |
| *B01J 37/08* | (2006.01) |
| *B01J 37/30* | (2006.01) |
| *B01J 23/835* | (2006.01) |
| *B01J 29/04* | (2006.01) |
| *B01J 29/40* | (2006.01) |
| *B01J 37/00* | (2006.01) |
| *B01J 37/02* | (2006.01) |
| *C10G 45/70* | (2006.01) |
| *C07C 5/41* | (2006.01) |

(52) U.S. Cl.
CPC ............. *B01J 29/44* (2013.01); *B01J 23/835* (2013.01); *B01J 29/047* (2013.01); *B01J 29/40* (2013.01); *B01J 37/0018* (2013.01); *B01J 37/0201* (2013.01); *B01J 37/08* (2013.01); *B01J 37/30* (2013.01); *C07C 5/41* (2013.01); *C10G 45/70* (2013.01); *C07C 2521/08* (2013.01); *C07C 2529/44* (2013.01); *C10G 2400/30* (2013.01); *Y02P 20/52* (2015.11)

(58) Field of Classification Search
CPC ......... B01J 29/064; B01J 29/068; B01J 29/44
USPC .................................................. 502/74, 77
See application file for complete search history.

(56) References Cited

U.S. PATENT DOCUMENTS

| | | | |
|---|---|---|---|
| 3,702,886 A | 11/1972 | Argauer et al. | |
| 4,104,320 A | 8/1978 | Bernard et al. | |
| 4,278,827 A | 7/1981 | Chu et al. | |
| 4,417,083 A | 11/1983 | Bernard et al. | |
| 4,435,283 A | 3/1984 | Buss et al. | |
| 4,485,185 A | 11/1984 | Onodera et al. | |
| 4,517,306 A | 5/1985 | Buss | |
| 4,595,669 A | 6/1986 | Fung et al. | |
| 4,645,586 A | 2/1987 | Buss | |
| 4,652,360 A | 3/1987 | Dessau | |
| 4,839,027 A | 6/1989 | Absil et al. | |
| 4,867,864 A | 9/1989 | Dessau | |
| 4,925,819 A | 5/1990 | Fung et al. | |
| 5,053,374 A | 10/1991 | Absil et al. | |
| 5,114,565 A | 5/1992 | Zones et al. | |
| 5,328,595 A | 7/1994 | Rainis | |
| 5,358,631 A | 10/1994 | Miller et al. | |
| 5,500,109 A | 3/1996 | Keville et al. | |
| 5,552,035 A | 9/1996 | Potter et al. | |
| 6,063,724 A | 5/2000 | Resasco et al. | |
| 6,365,767 B1 * | 4/2002 | Chang et al. | 558/277 |
| 6,709,570 B1 * | 3/2004 | Van Crijnen-Beers et al. | 208/111.01 |
| 6,784,333 B2 | 8/2004 | Juttu et al. | |
| 7,153,801 B2 | 12/2006 | Wu | |
| 7,582,583 B2 | 9/2009 | Bosch et al. | |
| 7,601,330 B2 | 10/2009 | Wang et al. | |
| 7,651,968 B2 | 1/2010 | Bosch et al. | |
| 7,745,675 B2 | 6/2010 | Ellis et al. | |

(Continued)

FOREIGN PATENT DOCUMENTS

| | | |
|---|---|---|
| CN | 101134171 B | 12/2010 |
| EP | 0145289 A2 | 6/1985 |

(Continued)

OTHER PUBLICATIONS

Otremba et al. ("Temperature-programmed Desorption of n-Propylbenzene from HNaZSM-5 and Na(Li, K, Rb, Cs)ZSM-5 Type Zeolites," Reaction Kinetics and Catalysis Letters 51(2), pp. 481-487, Dec. 1993).*

(Continued)

Primary Examiner — Melvin C Mayes
(74) Attorney, Agent, or Firm — Cantor Colburn LLP (57) ABSTRACT

In one embodiment, a formed catalyst can comprise: a Ge-ZSM-5 zeolite; a binder comprising silica with 1 to less than 5 wt % non-silica oxides; less than or equal to 0.1 wt % residual carbon; 0.4 to 1.5 wt % platinum; and 4.0 to 4.8 wt % Cs; wherein the weight percentages are based upon a total weight of the catalyst. In one embodiment, a method of making a formed catalyst can comprise: mixing an uncalcined Ge-ZSM-5 zeolite and a binder to form a mixture; forming the mixture into a formed zeolite; calcining the formed zeolite to result in the formed zeolite having less than or equal to 0.1 wt % of residual carbon; ion-exchanging the formed zeolite with cesium; depositing platinum on the formed zeolite; and heating the formed zeolite to result in a final catalyst; wherein the final catalyst comprises 4.0 to 4.8 wt % cesium and 0.4 to 1.5 wt % platinum.

20 Claims, 4 Drawing Sheets

(56) References Cited

U.S. PATENT DOCUMENTS

| | | | |
|---|---|---|---|
| 7,893,311 B2 | 2/2011 | Takamatsu et al. | |
| 7,902,103 B2 | 3/2011 | Beekman et al. | |
| 7,902,413 B2 | 3/2011 | Stevenson et al. | |
| 7,906,696 B2 | 3/2011 | Juttu et al. | |
| 8,119,551 B2 | 2/2012 | Stevenson et al. | |
| 2008/0255398 A1* | 10/2008 | Stevenson et al. | 585/407 |
| 2008/0293989 A1 | 11/2008 | Khanmamedova et al. | |
| 2008/0293990 A1 | 11/2008 | Stevenson et al. | |
| 2009/0156871 A1 | 6/2009 | Khare | |
| 2011/0132804 A1 | 6/2011 | Stevenson et al. | |
| 2011/0192766 A1 | 8/2011 | McCarthy et al. | |
| 2013/0296625 A1 | 11/2013 | Ghosh et al. | |
| 2014/0080696 A1 | 3/2014 | Ghosh et al. | |

FOREIGN PATENT DOCUMENTS

| | | |
|---|---|---|
| EP | 1115657 B1 | 5/2003 |
| GB | 1305137 A | 1/1973 |
| GB | 1356464 A | 6/1974 |
| WO | 8904860 A1 | 11/1988 |
| WO | 9413584 A1 | 6/1994 |
| WO | 2008153758 A2 | 12/2008 |
| WO | 2011068964 A1 | 6/2011 |

OTHER PUBLICATIONS

Vandegrift et al. ("The effect of test cylinder size on the compressive strength of sulfur capped concrete specimens," Highway Research Center and Department of Civil Engineering at Auburn University, Report IR-06-01, p. 1, Aug. 2006).*

International Search Report for International Application No. PCT/US2014/034504; International Filing Date: Apr. 17, 2014; dated Jul. 18, 2014; 5 pages.

Written Opinion of the International Search Report for International Application No. PCT/US2014/034504; International Filing Date: Apr. 17, 2014; dated Jul. 18, 2014; 6 pages.

CN 102039168 A English Abstract; Date of Publication: May 4, 2011; 2 pages.

CN102039165 A English Abstract; Date of Publication: May 4, 2011; 2 pages.

Hughes et al.; Aromatization of Hydrocarbons over Platinum Alkaline Earth Zeolites; Proceedings of 7 .sup.th International Zeolite Conference; Tokyo; pp. 725-732; 1986.

JP2004123412 A English Abstract; Date of Publication: Apr. 22, 2004; 1 page.

McVicker et al.; "Effect of Sulfur on the Performance and on the Particle Size and Location of Platinum in Pt/K Hexane Aromatization Catalysts"; Journal of Catalysis; vol. 139; pp. 46-61; 1993.

Tamm et al.; "Octane Enhancement by Selective Reforming of Light Paraffins"; Catalysis 1987; J.W. Ward (Editor); p. 335-353; 1988.

Tamm et al.; "Selective Catalytic Process for Conversion of Light Naphtha to Aromatics"; Energy Progress; vol. 7, No. 4; pp. 215-222; Dec. 1987.

* cited by examiner

METHOD OF PREPARING HYDROCARBON AROMATIZATION CATALYST, THE CATALYST, AND THE USE OF THE CATALYST

BACKGROUND

Descriptions of units, abbreviation, terminology, etc. used throughout the present disclosure are summarized in Table 1.

Zeolite is a crystalline hydrated aluminosilicate that can contain other metals in the framework of the zeolite crystal or that can be deposited, exchanged, or impregnated on the zeolite (i.e. on the surface or in the pores). A method for preparing a zeolite comprises (a) preparing an aqueous mixture of silicon oxide and sources of oxides of aluminum; and (b) maintaining said aqueous mixture under crystallization conditions until crystals of zeolite form. In the crystalline structure, there are pores and channels that can be interconnected. The dimensions and configuration of these pores and channels allow access by molecules of certain sizes. Zeolites are used as catalysts for, among other things, isomerization, toluene disproportionation, transalkylation, hydrogenation, alkane oligomerization, and aromatization. Aromatization is a multi-step process that can comprise the steps of dehydrogenation of the hydrocarbon, if the hydrocarbon is saturated, cyclization of the dehydrogenated hydrocarbon, and aromatization of the cyclized hydrocarbon.

One such example of hydrocarbon aromatization is aromatization of naphtha. Naphtha is a mixture mainly of straight-chained, branched, and cyclic aliphatic hydrocarbons, light naphtha having from five to nine carbon atoms per molecule and heavy naphtha having from seven to twelve carbon atoms per molecule. Typically, light naphtha contains naphthenes, such as cyclohexane and methylcyclopentane, and linear and branched paraffins, such as hexane and pentane. Light naphtha typically contains 60 to 99 wt % of paraffins and cycloparaffins. Light naphtha can be characterized as a petroleum distillate having a molecular weight range of 70 to 150 g/mol, a specific gravity range of 0.6 to 0.9 g/cm$^3$, a boiling point range of 50 to 320° F. (10 to 160° C.), and a vapor pressure of 5 to 500 mmHg at room temperature. Light naphtha can be obtained from crude oil, natural gas condensate, or other hydrocarbons streams by a variety of processes, e.g., distillation.

A zeolite can be formed into a catalyst by first forming the zeolite into a shaped zeolite body (e.g., an extrudate) and then further modifying the shaped zeolite (e.g., ion-exchange, metal deposition) to make a catalyst. Alternatively, the zeolite can first be modified (e.g., ion-exchange, metal deposition) and then the modified zeolite can be formed into a shaped catalyst. Forming a shaped zeolite body or shaped zeolite catalyst can be accomplished by binding the zeolite with a refractive oxide or combination of oxides such as $Al_2O_3$, $SiO_2$, $SiO_2$—$Al_2O_3$, and the like, where, depending on the catalytic reaction for which the catalyst is to be used, certain refractive oxide materials may be preferred over others. For example, a silica binder or a substantially silica containing binder can be used instead of an alumina binder for aromatization reactions. However, such a silica binder may not provide the catalyst with a desired mechanical strength, which can result in deterioration of catalyst integrity for use in commercial reactors.

The mechanical strength of a formed catalyst (e.g., an extruded catalyst) can be measured to ensure its ability to retain physical integrity during its use in a reactor. There are several methods used for measuring catalyst strength. One such method includes measuring flat crush strength by placing a piece between two flat surfaces, applying a compressive load, and measuring the force required to crush the piece. Flat crush is reported as pound force per millimeter (lbf/mm) or pound per millimeter (lb/mm).

Silica-bound formed zeolite catalysts for use in applications, such as the aromatization of light naphtha, often display low or unacceptable mechanical strength for use in certain commercial reactors, for example, less than 2.0 lb/mm for cylinder (⅛-inch (3.2 mm) diameter) shaped extruded catalyst. A zeolite catalyst with improved mechanical strength and a method of making would therefore be desirable. A zeolite with one or both of improved selectivity and conversion for naphtha aromatization would also be desirable.

BRIEF SUMMARY

Disclosed herein are catalyst, methods for making and using the same.

In one embodiment, a formed catalyst can comprise: a Ge-ZSM-5 zeolite; a binder comprising silica with 1 to less than 5 wt % non-silica oxides; less than or equal to 0.1 wt % residual carbon; 0.4 to 1.5 wt % platinum; and 4.0 to 4.8 wt % Cs; wherein the weight percentages are based upon a total weight of the catalyst.

In one embodiment, a method of making a formed catalyst can comprise: mixing an uncalcined Ge-ZSM-5 zeolite and a binder to form a mixture; forming the mixture into a formed zeolite; calcining the formed zeolite to result in the formed zeolite having less than or equal to 0.1 wt % of residual carbon; ion-exchanging the formed zeolite with cesium; depositing platinum on the formed zeolite; and heating the formed zeolite to result in a final catalyst; wherein the final catalyst comprises 4.0 to 4.8 wt % cesium and 0.4 to 1.5 wt % platinum.

In one embodiment, a method of making aromatic compounds from a naphtha feedstock can comprise: contacting the naphtha feedstock with any of the above catalysts; and aromatizing compounds in said naphtha feedstock.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

TABLE 1

| Abbreviation | Description |
|---|---|
| Å | angstrom |
| BTX | benzene, toluene, xylene |
| cm³/min | cubic centimeter per minute |
| ° C. | degree Celsius |
| ° F. | degree Fahrenheit |
| g | gram |
| g/cm³ | gram per cubic centimeter |
| g/h | gram per hour |
| g/mol | gram per mole |
| h | hour |
| lb/mm | pound per millimeter |
| lbf/mm | pound force per millimeter |
| mL/min | milliliter per minute |
| mL/g | milliliter per gram |
| mm | millimeter |
| mmHg | millimeter of mercury |
| m²/g | meter square per gram |
| mol % | mole percent |
| M | molar |
| MW | molecular weight |
| nm | nanometer |
| ppm | parts per million by weight |
| psia | pound per square inch absolute |
| SCCM | standard cubic centimeter per minute |
| vol % | volume percent |
| XRF | X-ray fluorescence |
| wt % | weight percent |

The present disclosure is directed to a catalyst and a method of preparing a catalyst that has one or more of increased crush strength, increased conversion for light naphtha aromatization, and increased selectivity for light naphtha aromatization. The catalyst can be a formed zeolite catalyst that has low residual carbon levels thereon, i.e. less than or equal to 0.1 wt %, and can exhibit flat crush strengths of greater than or equal to 2.0 lb/mm, specifically, greater than or equal to 2.4 lb/mm. As used herein the flat crush strength or crush strength is a measurement of mechanical strength of a shaped zeolite having a cylindrical shaped extrudate with a ⅛ inch (3.175 mm) diameter. The catalyst can be a germanium (Ge) substituted medium pore zeolite, which can be further modified to be non-acidic (for example by ion-exchanging with a base such as cesium), onto which a noble metal, such as platinum, has been deposited. The catalyst can be prepared by 1) forming a zeolite mixture into a shaped body (e.g., ⅛ inch (3.175 mm) cylindrical shaped extrudate), 2) calcining the shaped zeolite body, for example, such that the residual carbon levels are less than or equal to 0.1 wt %, where the shaped zeolite body can have a flat crush strength of greater than or equal to 2.0 lb/mm, 3) base-exchanging the formed zeolite body, 4) depositing a noble metal on the formed zeolite, and 5) heating the metal deposited formed zeolite body.

The zeolite can be any of a number of zeolites, where zeolites are crystalline aluminosilicates with a three-dimensional framework containing silica ($SKI_4$) and alumina ($AlO_4$) tetrahedra and can be naturally occurring or synthesized. Zeolite can contain elements other than aluminum and silicon in the crystalline framework. The term "zeolite" includes not only aluminosilicates, but substances in which the aluminum is replaced by other trivalent elements, and substances in which silicon is replaced by other tetravalent elements. Generally, zeolites are structures of $TO_4$ tetrahedra, which form a three dimensional network by sharing oxygen atoms where T represents tetravalent elements such as silicon, and trivalent elements such as aluminum. Zeolites are known catalysts for isomerization, toluene disproportionation, transalkylation, hydrogenation and alkane oligomerization and aromatization. Some zeolite catalysts, especially those containing a Group VIII deposited metal, can be susceptible to sulfur poisoning.

Examples of the zeolite structure are MTW, FER, MEL, TON, MRE, MWW, MFI, BEA, MOR, LTL, or MTT. The term "ZSM-5" is used in this specification to mean a zeolite having a MFI structure.

A germanium zeolite includes silicon, germanium, and optionally aluminum in the crystalline framework of the zeolite structure, for example, the germanium zeolite can be an aluminosilicate zeolite having germanium in the framework and can specifically be a germanium ZSM-5 (Ge-ZSM-5) zeolite. The germanium zeolite can comprise a medium pore zeolite having an average pore size of 5 to 7 Å, a $Si/Al_2$ atomic ratio of 40 to infinity ($\infty$), and a germanium content of 0.1 to 10 wt %. The germanium zeolite can comprise a zeolite having a structure such as MTW, FER, MEL, TON, MRE, MWW, MFI, BEA, MOR, LTL, and MTT.

Zeolites can have a $SiO_2/Al_2O_3$ mole ratio (SAR) of greater than or equal to 40, e.g., 40 to $\infty$, specifically, 50 to 300. Zeolites are generally catalytically active due to acidic sites on and within the zeolitic framework. Zeolites can be rendered non-acidic through a process of exchanging acidic hydrogen atoms with alkali or alkaline earth metal. These so-called base-exchanged zeolites are non-acidic or substantially non-acidic. Examples of alkali metals include sodium (Na), potassium (K), rubidium (Rb), cesium (Cs), and combinations comprising at least one of the foregoing. Examples of alkaline earth metals include magnesium (Mg), calcium (Ca), strontium (Sr), barium (Ba), and combinations comprising at least one of the foregoing. The alkali metals and alkaline earth metals are non-framework. These metals, alkaline earth metals and alkali metals, can be non-framework metals. For example, if the alkaline earth metals and/or alkali metal(s) are present in the zeolite, they can be present within the channels of the zeolite, and not as part of the framework.

The zeolite can be from a family of pentasil zeolites that contain five membered ring units or pentasil units in the framework structure. Such zeolites include ZSM-5, ZSM-11, ZSM-23, ferrierite, mordenite, silicalite, and so on. Silicalite, which contains an isotypic framework of ZSM-5, can also be included. The zeolite can be ZSM-5 or MFI (International Zeolite Association nomenclature of ZSM-5). The ZSM-5 zeolite has two-dimensional pore structure with straight channels (5.4 Å×5.6 Å) which are intersected by sinusoidal channels (5.1 Å×5.7 Å) with a maximum diameter of 9 Å at the intersection. The ZSM-5 zeolite catalysts and their preparation are described, for example, in U.S. Pat. No. 3,702,886. Such ZSM-5 zeolites are aluminosilicates that contain both silicon and aluminum in the crystalline structure. ZSM-11 is another pentasil aluminosilicate zeolite that is similar to ZSM-5.

The zeolite can further contain elements other than aluminum and silicon in the crystalline framework, where at least some of the aluminum can be replaced by other trivalent elements and/or at least some of the silicon can be replaced by other tetravalent elements. Generally, zeolites are structures of $TO_4$ tetrahedra, which form a three dimensional network by sharing oxygen atoms where T represents tetravalent elements, such as silicon, and trivalent elements, such as aluminum. Tetravalent elements, such as germanium, tin, lead, zirconium, titanium, vanadium, or chromium, can be substituted for the silicon. Trivalent elements, such as gallium, boron, indium, thallium, or iron, can be substituted for the aluminum. These tetravalent and trivalent elements would be in the framework of the zeolite crystal. Other elements which can be in the framework of the zeolite crystal are zinc or phosphorus. The zeolite can comprise germanium and can be a Ge-ZSM-5 zeolite. The germanium content of the zeolite can be 1.0 to 10.0 wt %, specifically, 3.5 to 6.0 wt %.

The zeolite can be formed into a shaped body by extruding a mixture comprising a zeolite powder; a binder, which can comprise a solid silica (such as attapulgite, e.g. Min-U-Gel™ commercially available from Active Minerals International, Ultrasil™ commercially available from Degussa Corporation, and Davisil™-643 commercially available from Sigma-Aldrich) and/or a colloidal silica (such as an ammonium ion stabilized colloidal silica e.g. Ludox™ AS-30, Ludox™ AS-40, Ludox™ SM-30, Ludox™ HS-30, Nalco™ 1034A, available from Nalco Company, or those available from Sigma-Aldrich), wherein the colloidal silica can comprise 30 to 40 wt % silica; an extrusion aid (such as polyvinyl alcohol or polyacrylamide); or a combination comprising one or more of the foregoing. The binder can comprise inorganic oxide materials. The binder can comprise an aluminum- or silicon-containing material such as silica, alumina, clay, aluminum phosphate, silica-alumina, or combinations comprising at least one of the foregoing. The binder can comprise oxides of magnesium, titanium, zirconium, thorium, silicon, boron, and mixtures thereof; a clay, e.g., kaolin or montmorillonite; carbon, e.g., carbon black, graphite, activated carbon, polymers or charcoal; a metal carbide or nitride, e.g., molybdenum carbide, silicon carbide or tungsten nitride; a metal oxide hydroxide, e.g., boehmite; or a combination comprising one or more of the foregoing. The binder can comprise 0.5 to 15 wt %, specifically, 1 wt % to less than 5 wt %, more specifically, 1 to 4.5 wt % non-silica oxides. The binder can comprise a colloidal silica binder, where the colloidal silica binders are acid, $NH_4^+$, or $Na^+$ stabilized colloidal silicas. The binder can comprise a solid silica that can comprise a crystalline silica, an amorphous silica, or a combination thereof. The binder can comprise at least one colloidal silica binder and at least one solid silica ($SiO_2$) binder.

The binder can have a particle size of 10 to 25 nm. The binder can comprise a mixture of one or more binders and can comprise at least one solid binder and a mixture of colloidal binders, the mixtures of colloidal binders can include at least 10 wt % of a colloidal binder, e.g., having particle sizes of 10 to 30 nm, while the remaining colloidal binders can, for example, have particle sizes of 1 to 30 nm. The binder can comprise a mixture of at least 20 wt % of a colloidal binder, e.g., having a particle size of 10 to 30 nm, while the remaining binders can have particle sizes of 5 to 10 nm. The binder can have a surface area less than or equal to 250 $m^2$/g, specifically, 250 to 100 $m^2$/g.

The binder can be present in the catalyst in an amount of up to 99 wt %, e.g., 1 to 99 wt %, specifically, 10 to 60 wt % based on the total weight of the final catalyst. The catalyst can comprise 15 to 50 wt %, specifically, 20 to 40 wt % of silica-containing binder material.

The extrusion aid can comprise a partially hydrolyzed polyvinyl alcohol and can be produced commercially by hydrolysis of polyvinyl acetate. When polyvinyl acetate is hydrolyzed the acetate groups ($COCH_3$) are substituted by hydrogen to form alcohol (OH) groups along the polymer chain. Hereinafter, the term 'partially hydrolyzed' refers to a polyvinyl acetate that has been hydrolyzed by less than or equal to 90%. In the partially hydrolyzed polyvinyl alcohol, acetate and alcohol groups are randomly distributed in the polymer chain. The partially hydrolyzed polyvinyl alcohol can have a weight average molecular weight (MW) of 500 to 500,000 g/mol, specifically, 10,000 to 200,000 g/mol. The partially hydrolyzed polyvinyl alcohol can be used in an amount of 0.1 to 5 wt %, specifically, 0.5 to 3 wt %, more specifically, 1 to 2 wt %, based on the total weight of the mixture.

The extrusion aid can comprise polyacrylamide. The polyacrylamide can have a weight average MW of 2 to 10 million g/mol, specifically, 2 to 7 million g/mol. The polyacrylamide can be used in an amount of 0.1 to 5 wt %, specifically 0.5 to 3 wt %, more specifically, 1 to 2 wt %, based on the total weight of the mixture. An example of a suitable commercially available source of polyacrylamide is that sold as under the trademark CYFLOC™ N-300 LMW Flocculant available from Cytec, West Peterson, N.J., which is a polyacrylamide having a MW of 2 to 5 million g/mol.

The shaped zeolite body (also referred to as the formed zeolite) can be formed by various forming processes such as pelletizing, tableting, extruding, and any other technique of forming a catalyst into a shape, as well as a combination comprising at least one of the foregoing processes. The resulting shaped zeolite body can be, for example, pellets and/or tablets. The shaped zeolite body can have cross-sections that are, for example, circular, oval, oblong, square, rectangular, diamond, polygonal, or a combination comprising one or more of the foregoing. Specific examples include cylindrically shaped extrudates, such as 1/16 inch (1.6 mm) or 1/8 inch (3.2 mm) cylindrically shaped extrudates.

The formed zeolite can be calcined to burn off one or more of the zeolite structure directing agents, the extrusion aid, and any other decomposable materials that may be present. The formed zeolite can be calcined at a temperature of greater than or equal to 500° C., specifically, greater than or equal to 530° C., more specifically, greater than or equal to 550° C. The formed zeolite can be calcined at a temperature of 500 to 650° C. The formed zeolite can be calcined for greater than or equal to 0.5 h, specifically greater than or equal to 1 h, more specifically greater than or equal to 2 h. The formed zeolite can be calcined for 0.5 to 20 h.

The formed zeolite can be calcined at a temperature for a sufficient amount of time such that the residual carbon level on the formed zeolite is less than or equal to 0.3 wt %, specifically, less than or equal to 0.1 wt %, more specifically, less than or equal to 0.05 wt %. For example, the formed zeolite can be calcined at 500 to 530° C. for greater than or equal to 11 hours, at greater than 530° C. to less than 650° C. for 1 to 11 hours, or at greater than or equal to 550° C. for greater than or equal to 2 hours. The Applicants surprisingly found that reducing the level of residual carbon on the formed zeolite resulted in an improvement in the mechanical strength, specifically, the crush strength of the resultant catalyst. Furthermore, it was surprisingly found that the crush strength was not negatively impacted upon calcining the formed zeolite at temperatures of 550 to 650° C.

The formed zeolite can then be subjected to one or both of ion-exchange with a base (also referred to as base-exchange) and deposition of a noble metal to result in a catalyst. The formed zeolite can be base-exchanged with an alkali metal or alkaline earth metal to reduce acidity. The base-exchange can occur before, during, or after deposition of the noble metal.

The formed zeolite can be base-exchanged with an alkali metal or alkaline earth metal, such as cesium, potassium, sodium, rubidium, barium, strontium, calcium, magnesium, lithium, and mixtures thereof, to reduce acidity. Accordingly, the resultant catalyst can be non-acidic, where one meaning of the term "non-acidic" should be taken to mean a catalyst which has been base-exchanged. The formed zeolite can be base-exchanged to the extent that most or all of the cations associated with aluminum are alkali metal or alkaline earth metal. An example of a monovalent base: aluminum molar ratio in the zeolite after base exchange is at least 0.9.

Likewise, the term "non-acidic" can mean an aluminum-free zeolite. An aluminum-free zeolite need not be base-exchanged to be non-acidic. The aluminum-free zeolite can contain another tetravalent or trivalent element, such as titanium, iron, gallium, boron, germanium, or tin. "Aluminum-free" zeolite has a meaning of having aluminum content of no more than 0.4 wt %. Within the meaning and for the purposes of the present disclosure, a zeolite can be "non-acidic" by ion-exchange with a base or by having a low aluminum content.

The formed zeolite can be ion-exchanged with a base by contacting a solution comprising a base with the zeolite. The solution can be a 0.01 to 1 M solution and it can contact (e.g., be flowed over or passed through a bed of) the formed zeolite for a sufficient amount of time to obtain the desired amount of base-exchange. For example, the formed zeolite can be base-exchanged with cesium by flowing a solution comprising a water soluble cesium compound (such as cesium nitrate, cesium chloride, and the like) over the zeolite extrudates such that the final amount of cesium in the zeolite (as determined by X-ray Fluorescence (XRF) technique) is 3.0 to 5 wt %, specifically, 4.0 to 4.8 wt %, more specifically, 4.0 to 4.6 wt %, more specifically, 4.0 to 4.5 wt % based on the total weight of the final catalyst. In other words, the ion-exchanging can comprise ion-exchanging to obtain 3.0 to 5 wt %, specifically, 4.0 to 4.8 wt %, more specifically, 4.0 to 4.6 wt %, more specifically, 4.0 to 4.5 wt % Cs in the final catalyst, based on the total weight of the final catalyst.

A noble metal can be deposited on the formed zeolite, for example by methods such as ion exchange, impregnation, and incipient wetness impregnation. The noble metal can be added to the formed zeolite as a noble metal compound (e.g., a noble metal salt) that readily dissolves in water. For example, when the metal is platinum, the platinum source can be any applicable platinum source, such as chloroplatinic acid ($H_2PtCl_6 \cdot 6H_2O$), tetraamine platinum nitrate ($(NH_3)_4Pt(NO_3)_2$), or a combination comprising at least one of the foregoing. The noble metal can be present in the catalyst in an amount of 0.05 to 3 wt % (as measured by XRF technique), specifically, of 0.15 to 2 wt %, and more specifically, of 0.15 to 1.5 wt %, and even more specifically, of 0.4 to 1.0 wt %. In other words, the process can comprise depositing to obtain 0.05 to 3 wt % (as measured by XRF technique), specifically, of 0.15 to 2 wt %, and more specifically, of 0.15 to 1.5 wt %, and even more specifically, of 0.4 to 1.0 wt % platinum in the final catalyst, based upon a total weight of the final catalyst. The noble metal can comprise palladium, silver, platinum, gold, iridium, rhodium, ruthenium, or a combination comprising one or more of the foregoing, specifically, the noble metal can comprise platinum.

The catalyst can be heat treated after one or both of ion-exchanging with a base and after noble metal deposition. The catalyst can be heated at an elevated temperature of greater than or equal to 200° C., specifically 200 to 400° C. for a period of time sufficient to decompose the metal salt. The heating time can be 0.5 to 10 h, specifically, 0.5 to 5 h. The catalyst can be further calcined, e.g., at a temperature of 200 to 400° C., specifically, 250 to 330° C., for a period of 0.5 to 20 h, specifically, 1 to 20 h, more specifically, 5 to 8 h. The heat treatment can be under air, $O_2$, $N_2$, $H_2$ or a combination comprising at least one of the foregoing.

The catalyst can concurrently function as one or more of an isomerization, a cracking, a dehydrogenation, a dehydrocyclization, and an aromatization catalyst. Specifically, the catalyst can be used in a process of aromatization of alkanes, such as alkanes having six to twelve carbon atoms per molecule, to produce aromatics, such as benzene, ethyl benzene, toluene, and xylene. The contact between the alkane and the catalyst can be at a liquid hourly space velocity of 0.1 to 100 l/h, at a temperature of 200 to 950° C., specifically, 425 to 650° C., more specifically, 450 to 625° C., even more specifically, 475 to 550° C., at a pressure of 5 to 315 psia. The feedstream to the reactor containing the catalyst may comprise greater than or equal to 30 vol % paraffins (e.g., greater than or equal to 50 vol % paraffins), and optionally low, (i.e. less than or equal to 20 vol %, or even less than or equal to 10 vol %) naphthenes. The feedstream to the reactor can comprise of hydrocarbons having any ratio of paraffin and naphthene hydrocarbons. The feedstream can comprise $C_{6-8}$ alkanes, either alone or as components in a mixture, i.e., in an amount of 0 to 100 vol % for each of $C_6$, $C_7$, and $C_8$ alkane.

The feedstream can be a naphtha feed. The naphtha feed can be a refinery product comprising greater than or equal to 25 wt %, specifically, greater than or equal to 35 wt %, more specifically, greater than or equal to 50 wt % of $C_{5-9}$ aliphatic and cycloaliphatic hydrocarbons such as olefins and paraffins, and zero to 40 wt % $C_{6-13}$ aromatics (e.g., zero to 20 wt % $C_{6-13}$ aromatics). The naphtha feed can comprise up to 1,000 ppm sulfur, specifically, 1 to 500 ppm sulfur, more specifically, 1 to 250 ppm sulfur, even more specifically 1 to 50 ppm sulfur, where the term sulfur refers to elemental sulfur as well as sulfur compounds such as organosulfides or heterocyclic benzothiophenes. The naphtha feed can comprise up to 100 ppm of nitrogen compounds. Aliphatic hydrocarbons that can be present in the naphtha feed include n-hexane, 2-methylpentane, 3-methylpentane, n-heptane, 2-methylhexane, 3-methylhexane, 3-ethylpentane, 2,5-dimethyl hexane, n-octane, 2-methylheptane, 3-ethylhexane, n-nonane, 2-methyloctane, 3-methyloctane, n-decane, the corresponding $C_{5-9}$ cycloparaffins, and combinations comprising one or more of the foregoing.

The following examples are provided to illustrate the improved catalyst. The examples are merely illustrative and are not intended to limit devices made in accordance with the disclosure to the materials, conditions, or process parameters set forth therein.

EXAMPLES

The materials used in the following examples are described in Table 2. Unless specifically stated otherwise, the materials are used in the form as set forth in Table 2, and the quantities identified in the examples are based upon that form.

TABLE 2

| Component | Source |
| --- | --- |
| Ge-ZSM-5[a] | Sud-Chemie |
| Min-U-Gel ™ [b] | Active Minerals Intl. |
| Colloidal silica, Ludox ™ AS-30 (30 wt % $SiO_2$ in aqueous solution) | Sigma-Aldrich |

TABLE 2-continued

| Component | Source |
|---|---|
| Polyacrylamide (Cyfloc™ N-300 LMW, MW 2-5 million g/mol) | Cytec |
| $CsNO_3$ | Sigma Aldrich |
| $(NH_3)_4Pt(NO_3)_2$ | Sigma Aldrich |
| n-Hexane (reagent grade, 99%+) | Sigma Aldrich |
| Deionized water | SABIC labs |

[a] As-synthesized (containing template); elemental analysis (by XRF method), Si = 38.08 wt %, Al = 0.69 wt %, Ge = 5.83 wt %, Na = 0.22 wt %, $Si/Al_2$ = 106.03, $Si/Ge_2$ = 33.76, $Si/(Al_2 + Ge_2)$ = 25.61.
[b] Min-U-Gel, Composition: (wt %): 66% $SiO_2$, 11.71% $Al_2O_3$, 9.70% MgO, 4.02% $Fe_2O_3$, 0.55% $TiO_2$, 0.99% $P_2O_5$, 2.92% CaO, 1.07% $K_2O$, 2.57% $CO_2$, 0.25% $SO_4$.

Examples 1-20

Zeolite Extrudate Formation, Residual Carbon, and Crush Strength

An extrudable mixture containing 3,200 g of as-synthesized Ge-ZSM-5 powder (containing structure directing agent), 488 g of Min-U-Gel, 3,267.6 g of Ludox™ AS-30, and 38.2 g of polyacrylamide was extruded into ⅛ inch diameter cylinder shaped zeolite extrudate. The zeolite extrudates contained 32.8 wt % binder after calcination, where the calcination profiles for each example are described in Table 3. In these examples, unless stated otherwise, zeolite, shaped zeolite body, shaped zeolite catalyst or powder zeolite catalyst were calcined or heat treated under an air environment. The formation of the extrudate was successfully scaled-up.

The calcined zeolite extrudates were analyzed for residual carbon (C) by combustion under pure $O_2$ up to 850° C. using a LECO™ C230. The residual C of the calcined zeolites is shown in Table 3 and in FIG. 1, where the diamonds are samples that were calcined for two hours and the squares are samples that were calcined for 11 hours.

The flat crush strength of the extrudates was measured without additional heating prior to the measurement using a Dilon SnapShot™ platform attached with Mecmesim™ AFG 500N advanced force gauge. The flat crush strength of each sample was measured by individually placing 10-12 pieces of extrudate, sized between 4 to 6 mm in length, on a flat plate and then applying a compressive load with a second flat plate to a piece of extrudate and measuring the force required to crush said extrudate between the two plates. The averaged value of force per unit of extrudate length (lb/mm) of the 10-12 measurements was used. The crush strength of the calcined zeolite extrudates are shown in Table 3 and in FIG. 2.

TABLE 3

| | Calcination Profile | | | |
|---|---|---|---|---|
| Example | Profile* | Maximum Temperature (° C.) | Time (h) | Residual Carbon (wt %) | Crush strength (lb/mm) |
| 1 | 1 | 510 | 2 | 0.292 | 2.27 |
| 2 | 1 | 510 | 2 | 0.285 | 2.18 |
| 3 | 1 | 510 | 11 | 0.121 | 2.50 |
| 4 | 2 | 530 | 2 | 0.184 | 2.03 |
| 5 | 2 | 530 | 5 | 0.105 | 2.45 |
| 6 | 2 | 530 | 11 | 0.100 | 2.06 |
| 7 | 2 | 530 | 5 | 0.105 | 2.45 |
| 8 | 2 | 540 | 2 | 0.141 | 1.99 |
| 9 | 2 | 540 | 11 | 0.078 | 2.66 |
| 10 | 2 | 550 | 2 | 0.082 | 2.59 |
| 11 | 2 | 550 | 11 | 0.047 | 2.47 |
| 12 | 3 | 550 | 2 | 0.092 | 2.47 |
| 13 | 3 | 550 | 2 | 0.100 | 2.31 |
| 14 | 4 | 550 | 2 | 0.093 | 2.34 |
| 15 | 5 | 550 | 2 | 0.101 | 2.58 |
| 16 | 3 | 550 | 1 | 0.112 | 2.01 |
| 17 | 2 | 575 | 2 | 0.037 | 2.61 |
| 18 | 2 | 600 | 2 | 0.032 | 2.62 |
| 19 | 6 | 650 | 2 | 0.003 | 2.46 |
| 20 | 4 | 650 | 2 | 0.010 | 2.69 |

*Profile 1: 5° C./min to 110° C. (2 h hold), 2° C./min ramp to 250° C. (30 min hold), 2° C./min to 350° C. (30 min hold), 2° C./min to specified max temperature with specified hold time.
Profile 2: 5° C./min to 120° C. (2 h hold), 2° C./min ramp to 260° C. (30 min hold), 2° C./min to 360° C. (30 min hold), 2° C./min to specified max temperature with specified hold time.
Profile 3: 5° C./min to 120° C. (30 m hold), 2° C./min ramp to 360° C. (30 min hold), 2° C./min to specified max temperature with specified hold time.
Profile 4: 5° C./min to 120° C. (1 h hold), 2° C./min to specified max temperature with specified hold time.
Profile 5: 2° C./min to specified max temperature with specified hold time.
Profile 6: 5° C./min to 120° C. (1 h hold), 2° C./min ramp to 360° C. (1 h hold), 2° C./min to specified max temperature with specified hold time.

Figure 1:
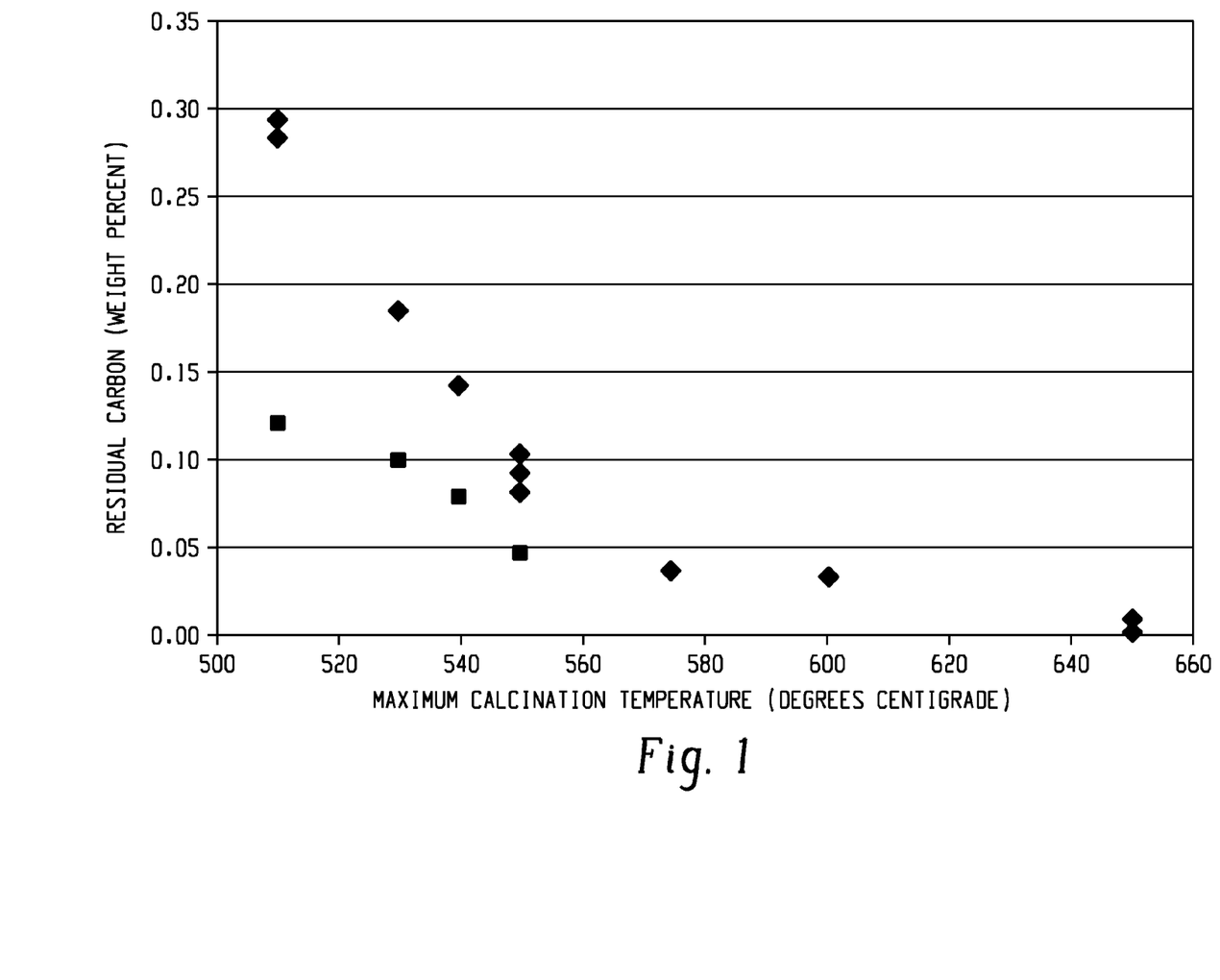
FIG. 1 is a graphical illustration of the maximum calcination temperature versus residual carbon levels of Examples 1-20, where the hold time at the maximum temperature is illustrated with squares for 11 h and diamonds for 2 h.

Table 3 and FIG. 1 show that all of the calcined zeolite extrudates in Examples 1-20 contained residual carbon in an amount of less than 0.3 wt %, where several of the examples contained less than about 0.1 wt % of residual carbon. The data shows that either or both of increasing the maximum calcination temperature or increasing the hold time results in a decrease in the amount of residual carbon on the zeolite extrudate. For example, a residual carbon amount of less than or equal to 0.1 wt % was achieved by calcining to a maximum temperature of 530° C. for greater than or equal to 11 h or by calcining to a maximum temperature of 550° C. for greater than or equal to 2 h.

Figure 2:
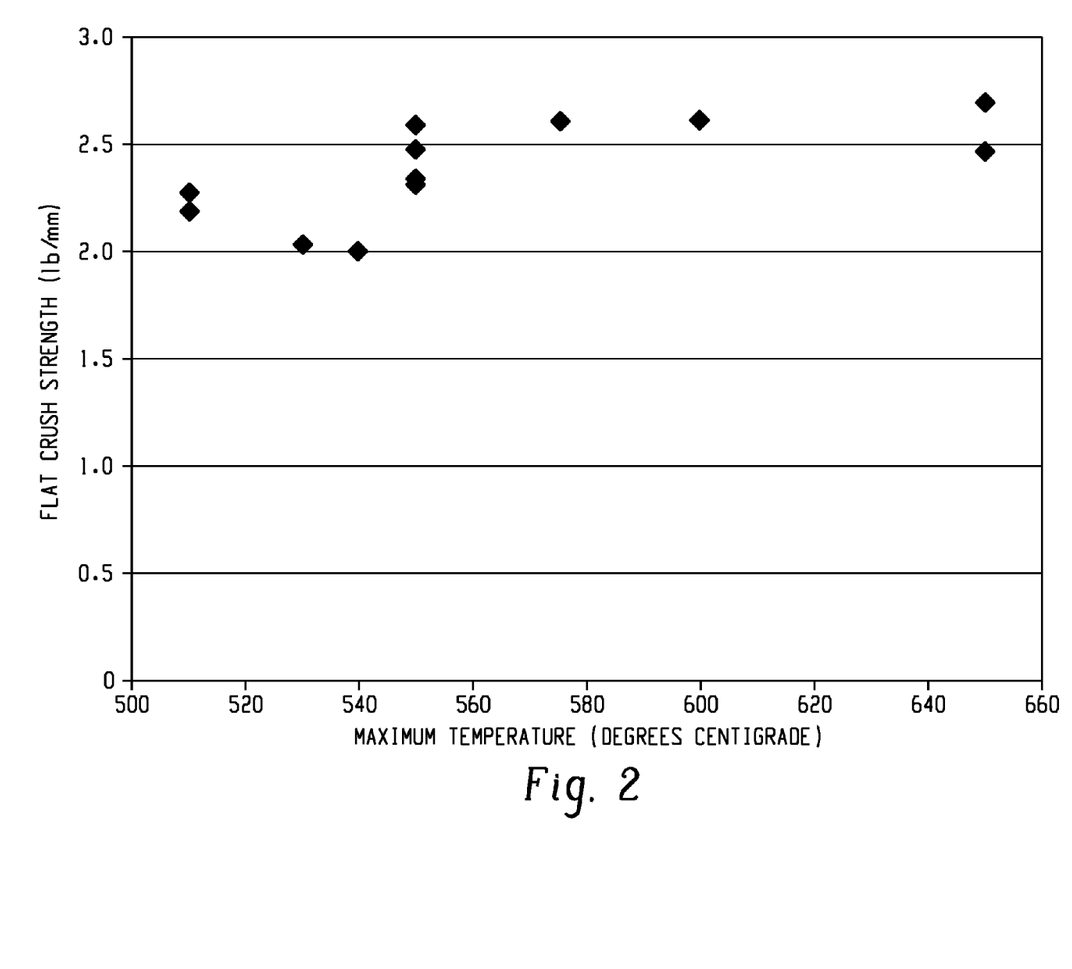
FIG. 2 is a graphical illustration of the maximum calcination temperature versus crush strength of Examples 1-20.

FIG. 2 is a plot of crush strength of zeolite extrudates versus residual carbon. The crush strength increased with the increase of (maximum) temperature up to about 550° C. above which the crush strength remained about the same. Importantly, the physical integrity of the extrudate, as measured by crush strength, was not negatively impacted upon heating the extrudate at greater than or equal to 550° C.

Examples 21-39

Base Exchange of the Zeolite Extrudate, Noble Metal Deposition, and Light Naphtha Aromatization Catalysts were prepared by first calcining the extrudates at 530° C. for 10 h [ramped (3° C./min) from room temperature to 120° C. held 3 h; ramped (4° C./min) to 350° C.; ramped (2° C./min) to 530° C. (held 10 h)]. Unless stated otherwise the calcined extrudates were then ion-exchanged with Cs by flowing a 0.1 M $CsNO_3$ solution at 5 mL/min (by maintaining the liquid levels above extrudate-bed) at room temperature for the duration as specified in Table 4, followed by washing with water, and calcining at 280° C. for 3 h. In Examples 38-39 different concentrations of $CsNO_3$ solution were used than in Examples 21-37.

TABLE 4

| Example | Extrudate (g) | Flow time (min) | Cs (wt %) | Pt (wt %) | Conversion (mol %) | Selectivity (mol %) |
|---|---|---|---|---|---|---|
| 21 | 10.1 | 10 | 2.35 | 0.66 | 10.6 | 83.8 |
| 22 | 10.1 | 20 | 2.84 | 0.68 | 13.4 | 87.2 |
| 23 | 10.1 | 40 | 3.67 | 0.69 | 16.9 | 91.2 |
| 24 | 10.0 | 60 | 4.15 | 0.64 | 17.6 | 92.9 |
| 25 | 10.1 | 60 | 4.14 | 0.63 | 18.2 | 93.0 |
| 26 | 10.3 | 90 | 4.85 | 0.64 | 17.4 | 92.6 |
| 27 | 9.5 | 90 | 4.62 | 0.66 | 17.1 | 92.9 |
| 28 | 10.0 | 120 | 5.01 | 0.62 | 15.0 | 91.3 |
| 29 | 10.3 | 60 | 4.47 | 0.63 | 17.8 | 93.0 |
| 30 | 10.2 | 75 | 4.52 | 0.62 | 16.8 | 92.8 |
| 31 | 30 | 60 | 4.28 | 0.65 | 17.8 | 92.8 |
| 32 | 30 | 60 | 4.04 | 0.66 | 17.6 | 92.8 |
| 33 | 30 | 90 | 4.43 | 0.72 | 17.4 | 92.6 |
| 34 | 100 | 75 | 4.17 | 0.65 | 17.6 | 93.0 |
| 35 | 100 | 75 | 4.15 | 0.64 | 17.3 | 92.7 |
| 36 | 100 | 75 | 4.29 | 0.62 | 17.2 | 92.8 |
| 37 | 100 | 75 | 4.15 | 0.69 | 17.3 | 92.7 |
| 38 | 100[a] | 75 | 4.86 | 0.63 | 12.0 | 91.2 |
| 39 | 100[b] | 75 | 5.30 | 0.62 | 11.1 | 89.1 |

[a] 0.18M CsNO$_3$ solution,
[b] 0.33M CsNO$_3$ solution

Figure 3:
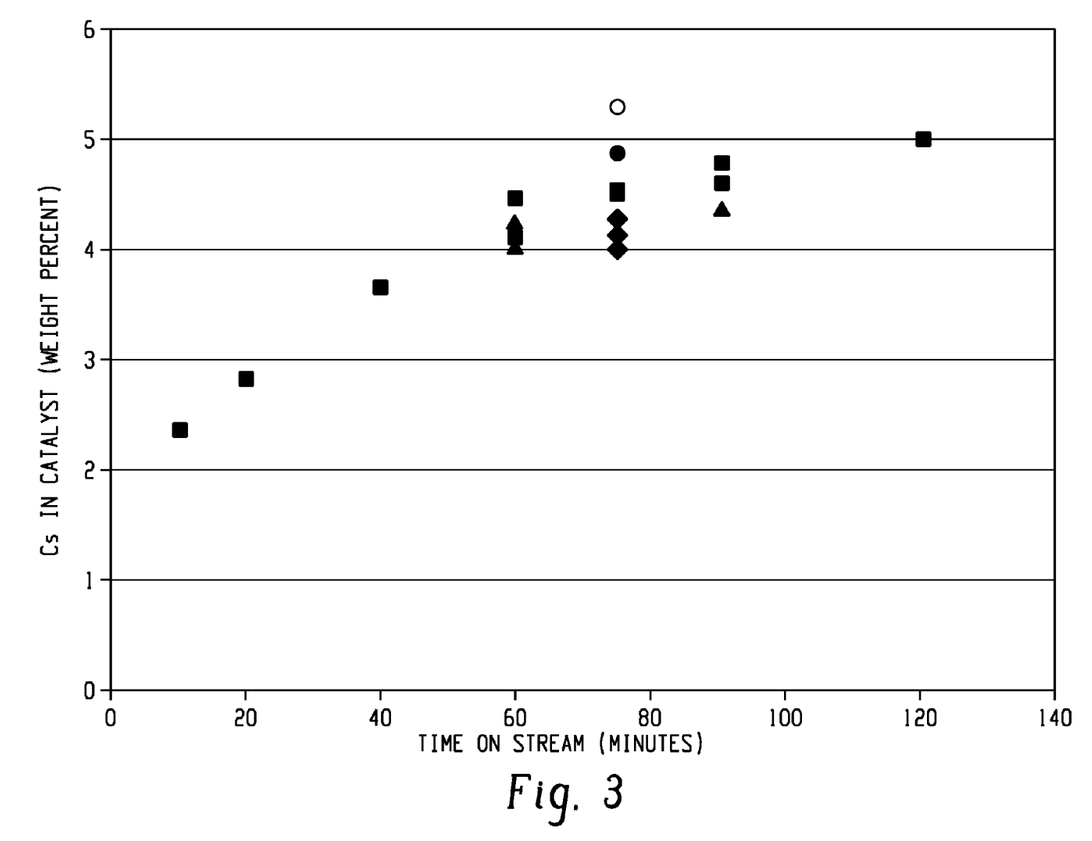
FIG. 3 is a graphical illustration of the time on stream (of $CsNO_3$ solution) versus cesium level of Examples 21-39.

Table 4 and FIG. 3 show that increasing time on stream results in an increase in the amount of cesium in the catalyst. Specifically, in FIG. 3, the squares refer to the 10 g extrudate samples, the triangles refer to the 30 g extrudate samples, the diamonds refer to the 100 g extrudate samples as described in Table 4. FIG. 3 further shows two 100 g extrudate samples that were prepared similar to Examples 34-37 except that the concentrations of the CsNO$_3$ were 0.18 M (filled circle) and 0.33 M (open circle).

Platinum was then impregnated onto the Cs-exchanged extrudates of Examples 21-39. Specifically, platinum was impregnated by the wet-incipient method where 1.163 g of (NH$_3$)$_4$Pt(NO$_3$)$_2$ solution containing 3.01 wt % Pt was diluted by adding water to make 2.50 g solution. The Pt-solution was then added onto 5.0 g of extrudate in a glass container. The container was capped and shaken gently for 2 hours. The cap was removed and the catalyst was left at room temperature to dry. The catalyst was calcined at 280° C. for 3 h. The resultant Pt content for the catalyst was from 0.62 to 0.72 wt % as shown in Table 3, where the Pt content as determined by XRF analysis is shown.

The catalysts of Examples 21-39 were then tested for light naphtha aromatization, where the catalysts were used for conversion of n-hexane to benzene under aromatization conditions. For comparison of the catalytic performance of each of the catalysts of Examples 21-39, a fixed load of fresh catalyst based on active catalyst (CsPt/Ge-ZSM-5) was used for each test run, where, specifically, 0.127 g of active catalyst was loaded in the reactor. (In the present application, the active catalyst refers to the quantity or percent zeolite present in the final catalyst. For example, if a catalyst contains 30 wt % binder then 0.127/(1-0.30) g or 0.181 g of the catalyst was loaded.) After loading and pressure testing, the testing unit was heated up to a temperature of 200° C. for 1 hour. A hydrogen gas flow of 25 SCCM was divided across the five reactor tubes. The temperature was then raised to 460° C. for 1 hour under the same hydrogen flow. Next, reagent grade n-hexane (99%+) was added at a flow rate of 7.14 g/h divided across the five reactors and the temperature raised to a temperature of 515° C. Reactor effluent was analyzed to determine the n-hexane conversion and selectivity. Conversion was defined as the fraction of n-hexane feed converted to benzene, $C_{1-5}$ products, and $C_{7+}$ products. Selectivity was defined as the sum of the amounts of benzene, toluene, and xylenes produced divided by the amount of feed converted to benzene, $C_{1-5}$ products, and $C_{7+}$ products. The resulting conversion and selectivity in mole percent (mol %) are shown in Table 4 and in FIG. 4 as diamonds and squares, respectively. The conversions and selectivities reported in this disclosure are at 50 h run time.

Figure 4:
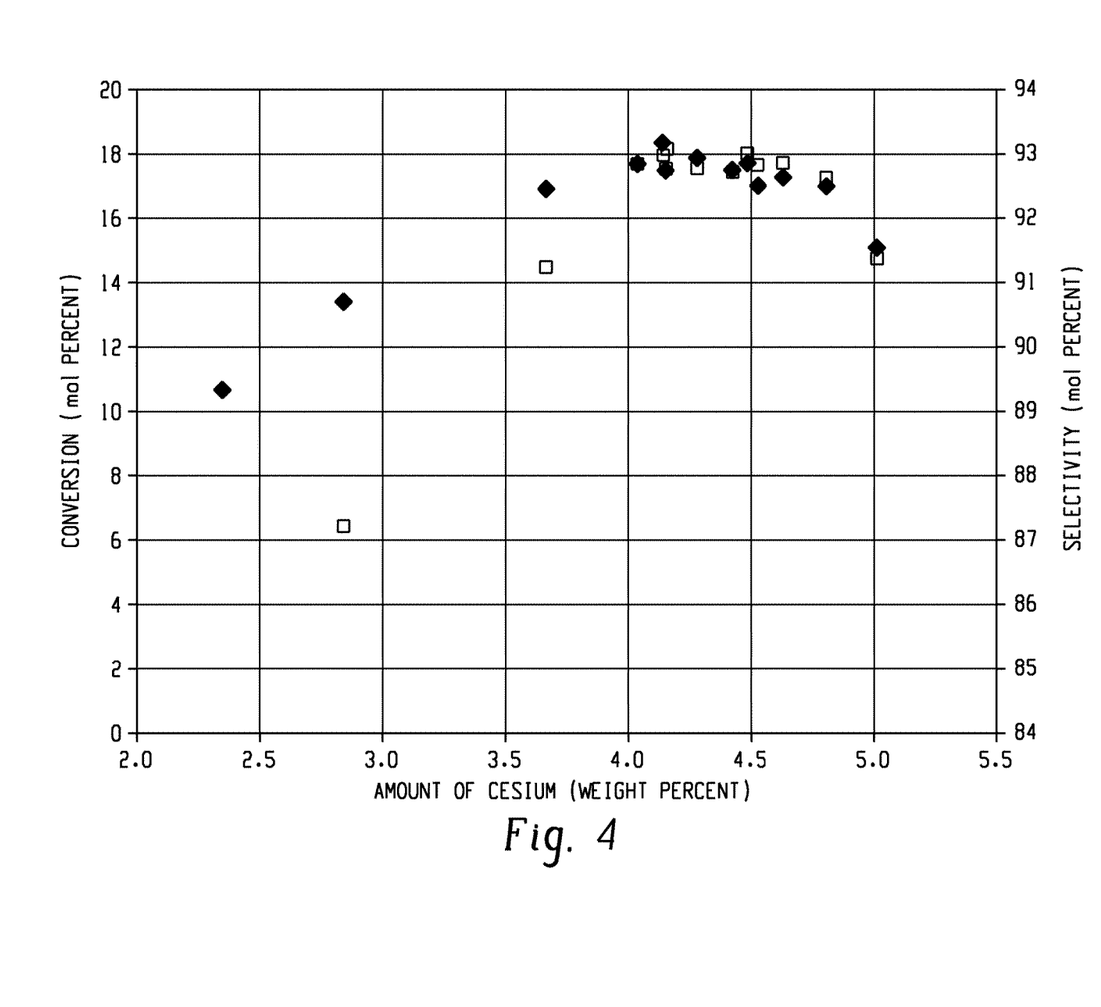
FIG. 4 is a graphical illustration of the cesium content in catalyst versus selectivity and conversion of Examples 21-39.

Table 4 and FIG. 4 show that catalysts containing 3.5 to 5.0 wt % Cs resulted in selectivities of greater than or equal to 91 mol % and conversions of greater than or equal to 14 mol % and that catalysts containing 4.0 to 4.8 wt % Cs resulted in selectivities of greater than or equal to 92 mol % and conversions of greater than or equal to 16 mol %. The formed catalysts showed equivalent activities and selectivities of the powder CsPt/Ge-ZSM-5 catalyst (Comparative Examples 47-1, 47-2).

Examples 40-46

Catalyst of Extrudates Calcined at 550 to 650° C.

In Examples 40-46, zeolite extrudates were calcined at 550° C. (Examples 40-44), 600° C. (Example 45), or 650° C. (Example 46) for 2 h and then Cs-exchanged and Pt-impregnated as described in Examples 21-39. The catalysts were tested for light naphtha aromatization reaction using the same conditions as described for Examples 21-39. The results are shown in Table 5, where Examples 40-44 exhibited crush strengths of significantly greater than 2.0 lb/mm, an average conversion of 18.2 mol %, and an average selectivity 93.1 mol %, which are comparable to powder CsPt/ZSM-5 catalyst (Examples 47-1, 47-2). Examples 45 and 46 exhibited similar crush strengths as Examples 40-46, an average conversion of 16.9 mol %, and an average selectivity 91.0 mol %.

TABLE 5

| Example | Profile[1] | Temp (° C.) | Crush strength (lb/mm) | Residual Carbon (wt %) | Cs (wt %) | Pt, (wt %) | Conv[2] (mol %) | Sel[3] (mol %) |
|---|---|---|---|---|---|---|---|---|
| 40 | 4 | 550 | 2.34 | 0.093 | 4.45 | 0.64 | 18.2 | 93.0 |
| 41 | 5 | 550 | 2.58 | 0.101 | 4.46 | 0.64 | 18.3 | 93.1 |
| 42 | 5 | 550 | 2.58 | 0.101 | 4.55 | 0.65 | 17.2 | 92.8 |
| 43 | 2 | 550 | 2.59 | 0.082 | 4.47 | 0.64 | 18.5 | 93.4 |
| 44 | 3 | 550 | 2.47 | 0.092 | 4.48 | 0.65 | 18.8 | 93.0 |
| 45 | 6 | 600 | 2.46 | n/a | 4.22 | 0.63 | 17.0[a] | 91.0[a] |
| 46 | 6 | 650 | 2.54 | 0.005 | 4.08 | 0.62 | 16.8[a] | 91.0[a] |

[1] See Profile in Table 3;
[a] Estimated from short runs;
[2] Conv is conversion; and
[3] Sel is selectivity

Comparative Examples 47-54

Crush Strengths and Aromatization Properties of Comparative Catalysts

Comparative CsPt/Ge-ZSM-5 catalysts were made as follows. As-synthesized Ge-ZSM-5 (400 g) was calcined at 530° C. for 10 h. About 200 g of the calcined Ge-ZSM-5 powder was ion-exchanged twice with a 0.5 M $CsNO_3$ solution at 100° C. The Cs-exchanged zeolite powder was heated at 300° C. for 10 h. 3.94 g of $(NH_3)_4Pt(NO_3)_2$ was dissolved in about 74 mL of deionized water and the solution was added to the Cs-exchanged Ge-ZSM-5 powder. The sample was subsequently calcined at 300° C. for 10 h to result in the CsPt/Ge-ZSM-5 powder catalyst of Comparative Example 47-1. Catalyst of Comparative Example 47-2 was a repeat preparation of Catalyst 47-1. Several batches of CsPt/Ge-ZSM-5 were made and mixed together to make about 2.5 kg of Catalyst 47-1. The mixed CsPt/Ge-ZSM-5 powder was then used to form Comparative Examples 48-54 as follows:

Comparative Catalyst 48: a mixture of 800 g CsPt/Ge-ZSM-5 powder catalyst, 120.8 g of Min-U-Gel™, 520 g of Ludox™ AS-30, and 16.8 g of polyacrylamide was extruded into ⅛ inch diameter cylindrical shaped catalyst and was further heated at 300° C. for 10 h (Method A).

Comparative Catalyst 49: a mixture of 40.05 g CsPt/Ge-ZSM-5 powder catalyst, 6.04 g of Min-U-Gel™, 38.30 g of Ludox™ AS-30, 0.84 g of polyacrylamide, and 1.9 g of deionized water was extruded into ⅛ inch diameter cylindrical shaped catalyst which was further heated at 300° C. for 10 h (Method A).

Comparative Catalyst 50: Comparative Catalyst 49 was further heated at 550° C. under 5% $H_2$ (balance $N_2$) (total flow rate 50 $cm^3$/min) for 2 h (Method B).

Comparative Catalyst 51: Comparative Catalyst 49 was further preactivated in-situ by heating at 510° C. under $H_2$ (5 $cm^3$/min) for 4 h prior to testing for aromatization reaction (Method C).

Comparative Catalyst 52: a mixture of 40.00 g powder CsPt/Ge-ZSM-5 catalyst, 6.04 g of Min-U-Gel™, 38.83 g of Ludox™ AS-30, and 0.84 g of polyacrylamide was extruded into ⅛ inch diameter cylindrical shaped catalyst and was further heated at 300° C. for 10 h (Method A).

Comparative Catalyst 53: Comparative Catalyst 52 was further calcined at 550° C. under 5% $H_2$ (balance $N_2$) (total flow rate 50 $cm^3$/min) for 2 h (Method B).

Comparative Catalyst 54: Comparative Catalyst 52 was preactivated in-situ by heating at 510° C. under $H_2$ flow (5 $cm^3$/min) for 4 h prior to testing for aromatization reaction (Method C).

The catalysts described above were tested for light naphtha aromatization reaction using the same conditions as described for Examples 21-39. The resulting catalysts, their crush strength, and aromatization properties are shown in Table 6, where the crush strength and aromatization properties were determined as described above.

TABLE 6

| Comparative Example | 47-1 | 47-2 | 48 | 49 | 50 | 51 | 52 | 53 | 54 |
|---|---|---|---|---|---|---|---|---|---|
| CsPt/Ge-ZSM-5 (g) | | | 800 | 40.05 | 40.05 | 40.05 | 40 | 40 | 40 |
| Min-U-Gel™ (g) | — | — | 120.8 | 6.04 | 6.04 | 6.04 | 6.04 | 6.04 | 6.04 |
| Ludox™ AS-30 (g) | — | — | 520 | 38.3 | 38.3 | 38.3 | 38.83 | 38.83 | 38.83 |
| Polyacrylamide (g) | — | — | 16.8 | 0.84 | 0.84 | 0.84 | 0.84 | 0.84 | 0.84 |
| Binder (wt %) | — | — | 24.8 | 29.8 | 29.8 | 29.8 | 30 | 30 | 30 |
| Cs, wt % | 5.02 | 5.43 | 3.79 | 3.74 | 3.74 | 3.74 | 3.57 | 3.57 | 3.57 |
| Pt, wt % | 0.95 | 0.82 | 0.78 | 0.78 | 0.78 | 0.78 | 0.75 | 0.75 | 0.75 |
| Method | | | A | A | B | C | A | B | C |
| Properties | | | | | | | | | |
| Crush strength (lb/mm) | n/a | n/a | 1.72 | 1.45 | 1.45 | 1.45 | 1.30 | 1.30 | 1.30 |
| Residual Carbon (wt %) | | | 0.198 | 0.154 | 0.036 | | 0.162 | 0.033 | |
| Conversion at 50 h (mol %) | 19.2 | 18.0 | 9.7 | 11.7 | 10.8 | 11.5 | 12.2 | 10.8 | 10.5 |
| Selectivity at 50 h (mol %) | 93.1 | 90.8 | 88.2 | 89.9 | 91.0 | 90.6 | 90.2 | 91.2 | 90.1 |

Table 6 shows that none of the Comparative Catalysts 48-54 were able to achieve crush strengths of greater than or equal to 2.0 lb/mm and were only able to achieve crush strengths of 1.30 to 1.72 lb/mm.

It was surprisingly discovered that the comparative catalysts (Examples 48, 49, and 52) formed differently than the catalysts in Examples 20-46, showed poor catalytic performances for light naphtha aromatization reaction. Furthermore, calcining at 550° C. ex-situ (Examples 50 and 53) or at 510° C. in-situ (Examples 51 and 54) under $H_2$ environment (to avoid any possible Pt agglomeration in air) resulted in no improvement in catalyst activity or selectivity.

Set forth below are some embodiments of the present catalyst, and methods of making and using the catalyst.

Embodiment 1

A formed catalyst comprising: a Ge-ZSM-5 zeolite; a binder comprising silica with 1 to less than 5 wt % non-silica oxides; less than or equal to 0.1 wt % residual carbon; 0.4 to 1.5 wt % platinum; and 4.0 to 4.8 wt % Cs; wherein the weight percentages are based upon a total weight of the catalyst.

Embodiment 2

A method of making a formed catalyst comprising: mixing an uncalcined Ge-ZSM-5 zeolite and a binder to form a mixture; forming the mixture into a formed zeolite; calcining the formed zeolite to result in the formed zeolite having less than or equal to 0.1 wt % of residual carbon; ion-exchanging the formed zeolite with cesium; depositing platinum on the formed zeolite; and heating the formed zeolite to result in a final catalyst; wherein the ion-exchanging comprises ion-exchanging to obtain 4.0 to 4.8 wt % cesium in the final catalyst; and wherein the depositing comprises depositing to obtain 0.4 to 1.5 wt % platinum in the final catalyst.

Embodiment 3

The method of Embodiment 2, wherein the calcining occurs at a temperature of greater than 500° C.

Embodiment 4

The method of any of Embodiments 2-3, wherein the calcining occurs at 500 to 530° C. for greater than or equal to 11 hours, at greater than 530 to less than 550° C. for 2 to 11 hours, or at greater than or equal to 550° C. for greater than or equal to 2 hours.

Embodiment 5

The method of any of Embodiments 2-4, wherein the heating occurs after one or both of after ion-exchanging with cesium and after depositing platinum.

Embodiment 6

The method of any of Embodiments 2-5, wherein the ion-exchanging with cesium occurs before, after, or during depositing platinum.

Embodiment 7

The method of any of Embodiments 2-6, further comprising adding an extrusion aid to the mixture.

Embodiment 8

The method of any of Embodiments 2-7, wherein forming the mixture into the formed zeolite comprises extruding the mixture.

Embodiment 9

The method of Embodiment 8, wherein extruding the mixture comprises extruding the mixture in a cylindrical shape.

Embodiment 10

The method of any of Embodiments 2-9, wherein the binder comprises: a colloidal silica comprising 20 to 40 wt % silica, based on the weight of the colloidal silica; and a solid silica comprising 10 to 40 wt % of a non-silica oxide, based on the weight of the solid silica.

Embodiment 11

The catalyst formed by the method of any of Embodiments 2-10.

Embodiment 12

The catalyst of any of Embodiments 1 and 11, wherein the zeolite comprises 1.0 to 10.0 wt % germanium in the framework.

Embodiment 13

The catalyst of any of Embodiments 1 and 11-12, wherein the catalyst comprises 4.0 to 4.6 wt % Cs.

Embodiment 14

The catalyst of any of Embodiments 1 and 11-13, wherein the catalyst comprises 4.0 to 4.5 wt % Cs.

Embodiment 15

The catalyst of any of Embodiments 1 and 11-14, wherein the form is cylindrical.

Embodiment 16

The catalyst of Embodiment 15, wherein the cylindrical form has a diameter of 1/16 inches (1.6 mm) to 1/8 inches (3.2 mm).

Embodiment 17

The catalyst of Embodiment 15, wherein the cylindrical form has a diameter of 1/8 inches (3.2 mm) or a diameter of 1/16 inches (1.6 mm).

Embodiment 18

The catalyst of any of Embodiments 1 and 11-17, wherein the formed catalyst has a flat crush strength of greater than 2.0 lb/mm, as determined on a 1/8 inch (3.2 mm) diameter cylindrical shaped extruded formed catalyst.

Embodiment 19

The catalyst of any of Embodiments 1 and 11-18, wherein the formed catalyst has a flat crush strength of greater than or equal to 2.4 lb/mm, as determined on a 1/8 inch (3.2 mm) diameter cylindrical shaped extruded formed catalyst.

Embodiment 20

The catalyst of any of Embodiments 1 and 11-19, wherein any Ge present in the final catalyst is in the framework, and/or any Cs present in the final catalyst is in the zeolite pores/channels but not in the framework.

Embodiment 21

The catalyst of any of Embodiments 1 and 11-20, wherein the binder comprises: a colloidal silica comprising 20 to 40 wt % silica, based on the weight of the colloidal silica; and 10 to 40 wt % solid silica, based on the weight of the binder.

Embodiment 22

The catalyst of any of Embodiments 1 and 11-21, wherein the binder comprises a solid silica.

Embodiment 23

The catalyst of Embodiment 22, wherein the solid silica comprises a crystalline silica, an amorphous silica, or a combination thereof.

Embodiment 24

The catalyst of any of Embodiments 1 and 11-23, wherein the binder comprises at least one colloidal silica binder and at least one solid silica binder.

Embodiment 25

The catalyst of any of Embodiments 1 and 11-24, comprising 15 to 50 wt % of silica-containing binder, based upon a total weight of the catalyst.

Embodiment 26

The catalyst of Embodiment 25, comprising 20 to 40 wt % of silica-containing binder.

Embodiment 27

The catalyst of any of Embodiments 21-26, The method of claim 18, wherein the colloidal silica comprises 30 to 40 wt % silica.

Embodiment 28

The catalyst of any of Embodiments 21-27, wherein the binder comprises 1 to less than 5 wt % non-silica oxides.

Embodiment 29

A method of making aromatic compounds from a naphtha feedstock comprising: contacting the naphtha feedstock with the catalyst of any of Embodiments 1 and 11-29; and aromatizing compounds in said naphtha feedstock.

Embodiment 30

The method of Embodiment 29, wherein the aromatizing comprises aromatizing n-hexane to benzene.

Embodiment 31

The method of Embodiment 30, comprising aromatization of the n-hexane to benzene at a selectivity of greater than or equal to 91 mol % and a conversion of greater than or equal to 14 mol %.

In general, the invention can alternately comprise, consist of, or consist essentially of, any appropriate components herein disclosed. The invention can additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A formed catalyst comprising:
   a Ge-ZSM-5 zeolite;
   a binder comprising silica with 1 to less than 5 wt % non-silica oxides;
   less than or equal to 0.1 wt % residual carbon;
   0.4 to 1.5 wt % platinum; and
   4.0 to 4.8 wt % Cs;
   wherein the weight percentages are based upon a total weight of the catalyst.

2. The catalyst of claim 1, wherein the zeolite comprises 1.0 to 10.0 wt % germanium in the framework.

3. The catalyst of claim 1, wherein the catalyst comprises 4.0 to 4.6 wt % Cs.

4. The catalyst of claim 1, wherein the catalyst comprises 4.0 to 4.5 wt % Cs.

5. The catalyst of claim 1, wherein the form is cylindrical.

6. The catalyst of claim 5, wherein the cylindrical form has a diameter of 1/16 inches (1.6 mm) to a diameter of 1/8 inches (3.2 mm).

7. The catalyst of claim 1, wherein the formed catalyst has a flat crush strength of greater than 2.0 lb/mm, as determined on a 1/8 inch (3.2 mm) diameter cylindrical shaped extruded formed catalyst.

8. The catalyst of claim 7, wherein the formed catalyst has a flat crush strength of greater than or equal to 2.4 lb/mm.

9. A method of making aromatic compounds from a naphtha feedstock comprising:
   contacting the naphtha feedstock with a catalyst, wherein the catalyst comprises
   a Ge-ZSM-5 zeolite;
   a binder comprising silica with 1 to less than 5 wt % non-silica oxides;
   less than or equal to 0.1 wt % residual carbon;
   0.4 to 1.5 wt % platinum; and
   4.0 to 4.8 wt % Cs;
   wherein the weight percentages are based upon a total weight of the catalyst; and
   aromatizing compounds in said naphtha feedstock.

10. The method of claim 9, wherein the aromatizing comprises aromatizing n-hexane to benzene.

11. The method of claim 10, wherein the aromatization of n-hexane to benzene has one or both of a selectivity of greater than or equal to 91 mol % and a conversion of greater than or equal to 14 mol %.

12. A method of making a formed catalyst comprising:
mixing an uncalcined Ge-ZSM-5 zeolite and a binder to form a mixture;
forming the mixture into a formed zeolite;
calcining the formed zeolite to result in the formed zeolite having less than or equal to 0.1 wt % of residual carbon;
ion-exchanging the formed zeolite with cesium;
depositing platinum on the formed zeolite; and
heating the formed zeolite to result in a final catalyst;
wherein the ion-exchanging comprises ion-exchanging to obtain 4.0 to 4.8 wt % cesium in the final catalyst; and
wherein the depositing comprises depositing to obtain 0.4 to 1.5 wt % platinum in the final catalyst.

13. The method of claim 12, wherein the calcining occurs at a temperature of greater than 500° C.

14. The method of claim 12, wherein the calcining occurs at 500 to 530° C. for greater than or equal to 11 hours, at greater than 530 to less than 550° C. for 2 to 11 hours, or at greater than or equal to 550° C. for greater than or equal to 2 hours.

15. The method of claim 12, wherein the heating occurs after one or both of after ion-exchanging with cesium and after depositing platinum.

16. The method of claim 12, wherein the ion-exchanging with cesium occurs before, after, or during depositing platinum.

17. The method of claim 12, wherein the mixture further comprises an extrusion aid.

18. The method of claim 12, wherein the binder comprises
a colloidal silica comprising 20 to 40 wt % silica, based on the weight of the colloidal silica; and
10 to 40 wt % a solid silica based upon the total weight of the binder.

19. The method of claim 18, wherein the colloidal silica comprises 30 to 40 wt % silica.

20. The method of claim 18, wherein the binder comprises 1 to less than 5 wt % non-silica oxides.

* * * * *